United States Patent
Riva et al.

(10) Patent No.: US 7,662,610 B2
(45) Date of Patent: Feb. 16, 2010

(54) SYNTHESIS OF INTERMEDIATES FOR THE PREPARATION OF PRAMIPEXOL

(75) Inventors: Sergio Riva, Seveso (IT); Paola Fassi, Vittuone (IT); Michele Scarpellini, Bergamo (IT); Pietro Allegrini, San Donato Milanese (IT); Gabriele Razzetti, Sesto S. Giovanni (IT)

(73) Assignee: Dipharma Francis s.r.l., Baranzate (IT)

( * ) Notice: Subject to any disclaimer, the term of this patent is extended or adjusted under 35 U.S.C. 154(b) by 454 days.

(21) Appl. No.: 11/622,259

(22) Filed: Jan. 11, 2007

(65) Prior Publication Data

US 2007/0166814 A1 Jul. 19, 2007

(30) Foreign Application Priority Data

Jan. 13, 2006 (IT) .......................... MI2006A0044

(51) Int. Cl.
*C12P 41/00* (2006.01)
(52) U.S. Cl. .................................................. 435/280
(58) Field of Classification Search ................... None
See application file for complete search history.

(56) References Cited

U.S. PATENT DOCUMENTS

| | | | |
|---|---|---|---|
| 4,731,374 A | 3/1988 | Griss et al. | |
| 4,843,086 A | 6/1989 | Griss et al. | |
| 4,886,812 A | 12/1989 | Griss et al. | |
| 4,981,862 A | 1/1991 | Schneider et al. | |
| 4,988,699 A | 1/1991 | Caprathe et al. | |
| 5,112,842 A | 5/1992 | Zierenberg et al. | |
| 5,650,420 A | 7/1997 | Hall et al. | |
| 6,727,367 B2 | 4/2004 | Pospisilik | |
| 6,770,761 B2 | 8/2004 | Pospisilik et al. | |
| 6,982,332 B2 | 1/2006 | Dutta | |

FOREIGN PATENT DOCUMENTS

| | | | |
|---|---|---|---|
| WO | WO 02098367 A3 | 12/2002 | |
| WO | 2005/092871 A2 | 10/2005 | |
| WO | WO 2006/012277 | * 2/2006 | |

* cited by examiner

*Primary Examiner*—Sandra E. Saucier
(74) *Attorney, Agent, or Firm*—Griffin & Szipl, P.C.

(57) ABSTRACT

A process for the preparation of an acid of formula (I), as the individual (R) enantiomer or (S), or a salt thereof

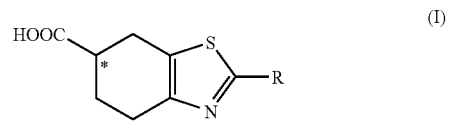

wherein R is a protected amino group; and the asterisk * denotes the stereogenic carbon atom, comprising contacting an ester of formula (II), as mixture of (R,S) enantiomers, or a salt thereof,

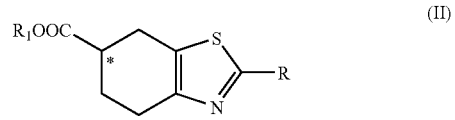

wherein $R_1$ is straight or branched $C_1$-$C_6$ alkyl, optionally substituted with phenyl; (the asterisk * and R defined above), with a lipase from *Candida antarctica*, under conditions effective to obtain a mixture comprising an acid of formula (I), as the individual (R) enantiomer, and an ester of formula (II), as the individual (S) enantiomer; the subsequent hydrolysis of the latter to obtain an acid of formula (I), as the individual (S) enantiomer; and, if desired, the conversion of an acid of formula (I), either as the (R) or (S) enantiomer, to a salt thereof.

13 Claims, No Drawings

SYNTHESIS OF INTERMEDIATES FOR THE PREPARATION OF PRAMIPEXOL

This application claims priority from IT Patent Application No. MI2006A000044, filed Jan. 13, 2006, the entire disclosure of which is incorporated herein reference.

FIELD OF THE INVENTION

The present invention relates to a novel method for the preparation of intermediates useful in the preparation of pramipexole and the use thereof in its preparation.

TECHNOLOGICAL BACKGROUND

Pramipexole, (S)-2-amino-6-n-propylamino-4,5,6,7-tetrahydro-benzothiazole, having formula (A),

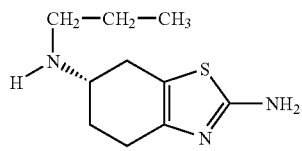
(A)

is a dopaminergic agonist, known from U.S. Pat. No. 4,843,086, used in the treatment of Parkinson's disease in the form of the dihydrochloride monohydrate.

WO 2005/092871 discloses the synthesis of pramipexole and the salts thereof, starting from a compound of formula (I), as a individual (S) enantiomer, or a salt thereof,

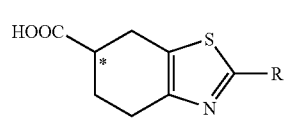
(I)

wherein R is a protected amino group; and the asterisk * denotes the stereogenic carbon atom. A compound of formula (I), as the individual (S) enantiomer, can be obtained by hydrolysis of a mixture of (R,S) enantiomers of an ester of formula (II), or a salt thereof,

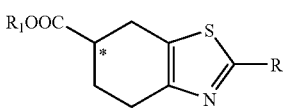
(II)

wherein $R_1$ is straight or branched $C_1$-$C_6$ alkyl, optionally substituted with phenyl; and the asterisk * and R are as defined above, followed by resolution of the mixture of (R,S) enantiomers of the acid of formula (I), resulting in the individual (S) enantiomer. Alternatively, an acid of formula (I), as the individual (S) enantiomer, can be obtained enzymatically from a mixture of (R,S) enantiomers of an ester of formula (II), or a salt thereof.

The higher the enantiomeric purity of the starting compound of formula (I), the higher will be the enantiomeric purity of the final product pramipexole, obtained in WO 2005/092871. Therefore, an acid of formula (I), or a salt thereof, as the individual (S) enantiomer in said process typically has an enantiomeric purity of at least approx. 96%, preferably of at least approx. 99%. The preparation of a compound of formula (I), or a salt thereof, with such a high purity degree requires a number of steps, such as hydrolysis, recovery of the racemic intermediate (I), salification with an optically active base, recovery of the salt optically active, recrystallization and deprotection of the optically active acid. From the industrial point of view, these operations involve longer production times and higher costs. To date, the enzymatic preparation is also problematic and cannot be applied industrially, as the most suited enzyme as well as the optimum reactions conditions for said substrate are difficult to ascertain.

There is therefore the need for an improved process for the conversion of an ester of formula (II), as a mixture of (R,S) enatiomers, to the individual (S) enantiomer of formula (I).

SUMMARY OF THE INVENTION

It has now been found an enzymatic process for the preparation of the intermediate of formula (I), as the individual (S) enantiomer, using the lipase from *Candida antarctica*, which fulfills the requirement for its production in industrial amounts.

According to the invention, an enzyme unit is the amount of enzyme which catalyzes the release of 1.0 μmol of fatty acid per minute from the corresponding triglyceride at 30° C. and pH=7.

DETAILED DISCLOSURE OF THE INVENTION

The object of the invention is a process for the preparation of an acid of formula (I), as the individual (R) or (S) enantiomer, or a salt thereof,

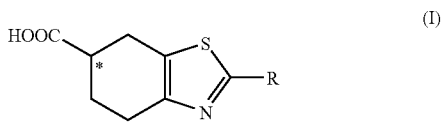
(I)

wherein R is a protected amino group, and the asterisk * denotes the stereogenic carbon atom, comprising contacting an ester of formula (II), as mixture of (R,S) enantiomers, or a salt thereof,

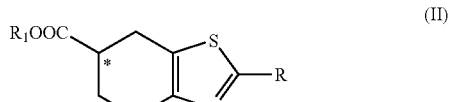
(II)

wherein $R_1$ is straight or branched $C_1$-$C_6$ alkyl, optionally substituted with phenyl; and the asterisk * and R have the meanings defined above, with a lipase from *Candida antarctica*, under conditions effective to obtain a mixture comprising an acid of formula (I), as the individual (R) enantiomer, and an ester of formula (II), as the individual (S) enantiomer; the subsequent hydrolysis of the latter to obtain an acid of formula (I), as the individual (S) enantiomer; and, if desired, the conversion of an acid of formula (I), either as the (R) or (S) enantiomer, to a salt thereof.

$R_1$ is preferably a $C_1$-$C_4$ alkyl group, e.g. methyl, ethyl, n-propyl, isopropyl, n-butyl, isobutyl or tert-butyl, more preferably ethyl or propyl; or benzyl or phenylethyl, in particular ethyl.

A group R can be, e.g., a protected amino group such as an acylamino, carbamoyl, arylmethylamino, phthalimido or silylamino group, as exemplified in WO 2005/092871. The acetylamino, propionylamino or pivaloylamino groups are preferred.

Examples of salts, preferably pharmaceutically acceptable, of a compound of formula (I) or (II) are reported in WO 2005/092871.

A lipase from *Candida antarctica* is preferably the lipase from *Candida antarctica* B, more preferably CAL B, expressed and produced in *Aspergillus oryzae*, marketed by Novozymes under the trade name Novozym®.

The enzyme can be either free or immobilized, typically marketed as Novozym® CALB-L or Novozym® 435.

The lipase from *Candida antarctica* surprisingly proved to be more advantageous than other enzymes which usually have catalytic effect in these reactions, under industrial conditions.

The following Table 1 compares the results obtained under the same conditions according to the invention, with different enzymes.

TABLE 1

| Enzyme | cosolvent v/v (20%) | ee acid (%) | c (%) | Time |
|---|---|---|---|---|
| Lipase from porcine Pancreas | DMF | N.A. | 8 | 12 h |
|  | DMF | N.A. | 27 | 4 gg |
| Chymotrypsin | DMF | N.A. | 3 | 12 h |
|  | DMF | N.A. | 11 | 4 gg |
| Lipase PS | DMF | N.A. | 0.3 | 16 h |
|  | DMF | N.A. | 2.1 | 3 gg |
| Lipase CV | DMF | N.A. | 0.3 | 16 h |
|  | DMF | N.A. | 2.5 | 3 gg |
| Lipase from Candida cylyndracea | DMF | 0 | 100 | 12 h |
|  | DMF | 15 | 82 | 2 h |
|  | DMF | 25 | 34 | 2 h |
| Lipasi CE-5 | DMF | 25 | 33 | 12 h |
|  | DMF | N.A. | 7 | 2 h |
| Esterase from porcine Liver | DMF | 0 | 99 | 12 h |

It should be noted that, when operating at longer times, most other enzymes do not promote the reaction, whereas in 2 cases (lipase from *Candida cylyndracea* and esterase from porcine liver) the reaction is non-specific, as it catalyzes the hydrolysis of both esters R and S of formula (II).

The reaction can be carried out in aqueous buffered solution at pH approx. ranging from 5.5 to 10.0; preferably ranging from approximately 6.0 to approximately 7.5. Examples of buffer solutions are TRIS [tris(hydroxymethyl)aminomethane]/HCl, buffer phosphate, ammonium bicarbonate, ethanolamine/HCl, sodium tetraborate($Na_2B_4O_7$)/HCl. The reaction is preferably carried out in the presence of a buffer phosphate or ammonium bicarbonate.

If desired, the reaction can be carried out in the presence of a cosolvent, e.g. a dipolar aprotic solvent, such as dimethylformamide, dimethylacetamide, acetonitrile, dimethylsulfoxide; a ketone, such as acetone or methyl-isobutyl ketone; an ether, such as tetrahydrofuran or dioxane; or a chlorinated solvent, for example dichloromethane; an apolar solvent, such as toluene or hexane; preferably the solvent is selected from dimethylformamide, tetrahydrofuran, acetonitrile, acetone, dimethylsulfoxide and dioxane, more preferably the cosolvent is tetrahydrofuran.

The volume ratio of buffered solution to cosolvent can approx. range from 1 to 10. and preferably approx. ranges from 1 to 3. It will be appreciated that the reaction does not require very diluted operative conditions, as is the case with usual enzymatic reactions, as the CAL B enzyme is surprisingly active even when the water to cosolvent ratio is not high. This results, on an industrial scale, in high volume productivity which allows to carry out the reaction in reactors of the size conventionally used in organic synthesis.

The reaction can be carried out at a temperature approximately ranging from 15 to 80° C., preferably approximately from 20 to 70° C., typically at 25° C.

The volume ratio of cosolvent—buffer mixture to substrate approximately ranges from 6 to 20 volumes, and preferably approximately from 8 to 15 volumes, in particular about 10 volumes.

The enzyme to substrate ratio approximately ranges from 1.0 to 10.0 U per mg of substrate, and preferably approximately from 1.0 U to 3.0 U per mg of substrate.

Reaction times can approximately range from 20 minutes to 48 hours, depending on the amount of enzyme used. As a rule, the reaction is continued until obtaining an about 50% conversion. Then the obtained precipitate of the (R) enantiomer of the acid of formula (I) is filtered, whereas the liquid phase contains the (S) enantiomer of the ester of formula (II).

Hydrolysis of the (S) enantiomer of the ester of formula (II) to give the individual (S) enantiomer of acid of formula (I) can be carried out by reaction with an alkali hydroxide, such sodium or potassium hydroxide, in amounts approximately from 1 to 4 equivalents, preferably approximately from 1.5 to 2.5 equivalents, in a polar protic solvent, for example water or a $C_1$-$C_4$ alkanol, in particular methanol, ethanol, i-propanol, or mixtures thereof; or mixtures thereof with a cosolvent as defined above; at a temperature approx. ranging from 0° C. to the solvent reflux temperature, preferably approximately from 10 to 50° C., in particular at 20° C.

An acid of formula (I), either as the (R) or (S) enantiomer, can be converted to a salt thereof with known methods.

According to the invention, the mixture of (R,S) enantiomers of an ester of formula (II) can contain the two individual enantiomers in any ratio to each other. The ratio of the individual (R) enantiomer of formula (I) and the individual (S) enantiomer of formula (II), present in the mixture obtainable according to the invention, is substantially related to the enantiomeric ratio in the starting ester of formula (II). A compound of formula (II), or a salt thereof, can be obtained by example according to U.S. Pat. No. 4,988,699 and WO 05/092871.

The enantiomeric purity is usually expressed as "enantiomeric excess" and defined as (S−R)/(R+S)×100. wherein S and R are respectively the amount of the (S) and (R) enantiomers. According to the invention, he term individual (S) or (R) enantiomer means that the enantiomeric purity is usually at least about 96%, preferably at least about 99%.

As stated above, a compound of formula (I), as the individual (S) enantiomer, is particularly useful in the preparation of pramipexol.

Therefore, the invention also provides a process for the preparation of pramipexole, or a pharmaceutically acceptable salt thereof, comprising:
  the rearrangement of a compound of formula (I), as the individual (S) enantiomer, or a salt thereof, thus obtained

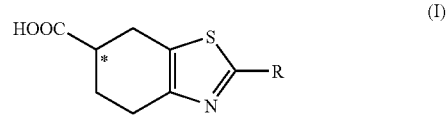

(I)

wherein R is a protected amino group and the asterisk *
denotes the stereogenic carbon atom, to obtain of a compound
of formula (III) as the individual (S) enantiomer

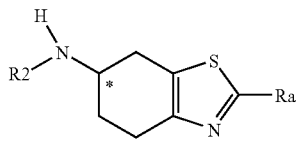

wherein Ra is an free or protected amino group, $R_2$ is
hydrogen or a group $R_3$—OR—CO—, wherein $R_3$ is straight
or branched $C_1$-$C_4$ alkyl and the asterisk * has the meaning
defined above, the alkylation of a compound of formula (III), to obtain a
compound of formula (IV)

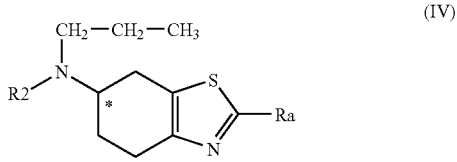

wherein Ra, $R_2$ and the asterisk * are as defined above, and,
if necessary, the removal of the protective group from the
primary amino group and/or of the $R_3$—OR—CO— group
from the secondary amino group, and, if desired, its conversion to a pharmaceutically acceptable salt thereof. Rearrangement of a compound of formula (I), as the individual (S)
enantiomer, or a salt thereof, the alkylation of a compound of
formula (III), and the conversion of pramipexol to a pharmaceutically acceptable salt thereof, can be carried out according to WO05/092871.

The following examples illustrate the invention.

EXAMPLE 1

Enzymatic resolution of an ester of formula (II), $R_1$=ethyl
and R=acetylamino, in various cosolvents.

The enzyme CAL B (0.3 mg) is dissolved in 800 μL of
buffer phosphate (pH=7.5; 0.05 M) then a solution of compound (II), wherein $R_1$ is ethyl and R is acetylamino (10 mg)
in a cosolvent (200 μL) is added. The reaction is left under
stirring at room temperature for a variable time, then is analyzed by HPLC.

The obtained results are reported in Table 2, in particular:
the general conversion of an ester of formula (II) to an acid of
formula (I), the enantiomeric excess of the resulting (R) acid
of formula (I), and the enantiomeric excess of the (S) ester of
formula (II).

TABLE 2

| Cosolvent | Time | ee %$_{acid\ (I)(R)}$ | ee %$_{ester\ (II)(S)}$ | Conversion |
|---|---|---|---|---|
| DMF | 30 min | 83 | 98 | 0.52 |
| THF | 3 h | 94 | 95 | 0.49 |
| $CH_3CN$ | 3 h | 89 | 100 | 0.53 |
| ACETONE | 3 h | 80 | 100 | 0.55 |
| DIOXANE | 3 h | 88 | 100 | 0.53 |

EXAMPLE 2

Enzymatic resolution of an ester of formula (II), $R_1$=ethyl,
R=acetylamino; in acetonitrile cosolvent with an immobilized lipase.

The immobilized enzyme CAL B (Novozym® 435) (0.5
mg) is suspended in 800 μL of buffer phosphate (pH=7.5;
0.05 M), then a solution of the compound of formula (II),
$R_1$=ethyl and R=acetylamino (10 mg) in acetonitrile (200 μL)
is added. The reaction is left under stirring at room temperature for 20 hours, then analyzed by HPLC.

The obtained results are reported in Table 3, in particular:
the general conversion of an ester of formula (II) to an acid of
formula (I), the enantiomeric excess of the resulting (R) acid
of formula (I), and the enantiomeric excess of the (S) ester of
formula (II).

TABLE 3

| Enzyme amount | time | ee %$_{acid\ (I)(R)}$ | ee %$_{ester\ (II)(S)}$ | Conversion |
|---|---|---|---|---|
| 0.5 mg | 20 h | 81 | 97 | 0.55 |

EXAMPLE 3

Preparation of (S)-2-acetylamino-4,5,6,7-tetrahydro-benzothiazole-6-carboxylic acid. (S) Enantiomer of the acid of
formula (I).

The enzyme CAL B (Novozym® CALB-L) (11 g) is added
to 25 ml of ammonium bicarbonate buffer (pH=8.0; 0.37 M),
then a solution of the compound of formula (II), $R_1$=ethyl and
R=acetylamino (5 g) in THF (25 ml) is added. The reaction is
left under stirring at room temperature for 24 hours, then THF
is evaporated off. The heterogeneous mixture is added with
25 ml of toluene, then heated to about 40° C., and the formed
acid (R) of formula (I) is filtered off. The filtrate is placed in
a separatory funnel, the phases are separated and the toluene
phase is recovered and added with a solution of NaOH (1 g) in
water (12 ml). The mixture is left under stirring for 5-10
hours, after that the aqueous phase is separated, washed with
toluene and acidified with acetic acid to approx. pH 5. The
formed precipitate is recovered by filtration and dried, to
obtain about 2 g of acid (S) of formula (I).

The invention claimed is:

1. A process for the preparation of an acid of formula (I),

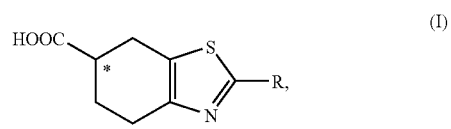

as an individual (R) enantiomer or (S) enantiomer, or a salt
thereof, wherein R is a protected amino group, and the asterisk *
denotes a stereogenic carbon atom, wherein the process
includes the steps of:

(a) providing an ester of formula (II), as a mixture of (R)
and (S) enantiomers, or a salt thereof,

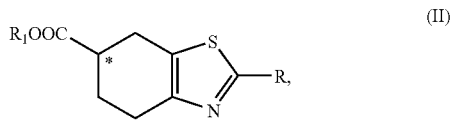

wherein $R_1$ is straight or branched $C_1$-$C_6$ alkyl, optionally substituted with phenyl, and the asterisk * and R have the meanings defined above; and (b) contacting the ester of formula (II) with a lipase from *Candida antarctica*, under conditions effective to obtain a mixture comprising an acid of formula (I), as individual (R) enantiomer, and an ester of formula (II), as individual (S) enantiomer; wherein subsequent hydrolysis of the ester of formula (II) obtains an acid of formula (I), as individual (S) enantiomer.

2. The process as claimed in claim 1, wherein the enzyme lipase from *Candida antarctica* is the lipase from *Candida antarctica* B.

3. The process as claimed in claim 1, wherein the contacting is carried out in a medium comprising an aqueous buffered solution at a pH ranging from approximately 5.5 to approximately 10.0.

4. The process as claimed in claim 3, wherein a buffer in the aqueous buffered solution is selected from the group consisting of tris(hydroxymethyl)aminomethane/HCl, phosphate, ammonium bicarbonate, ethanolamine/HCl and sodium tetraborate/HCl.

5. The process as claimed in claim 3, wherein the medium further comprises a cosolvent.

6. The process as claimed in claim 5, wherein the cosolvent is selected from the group consisting of a dipolar aprotic solvent, a ketone, an ether, a chlorinated solvent, and an apolar solvent.

7. The process as claimed in claim 5, wherein the volume ratio of buffered solution and to cosolvent ranges from approximately 1 to approximately 10.

8. The process as claimed in claim 5, wherein the volume ratio of cosolvent-buffered solution mixture to ester ranges from approximately 6 to approximately 20.

9. The process as claimed in claim 1, wherein the ratio of lipase to ester ranges approximately 1.0 to approximately 10.0 U per mg of ester.

10. The process, as claimed in claim 1, further comprising the steps of:
(c) reacting of the compound of formula (I), as the individual (S) enantiomer, or a salt thereof,

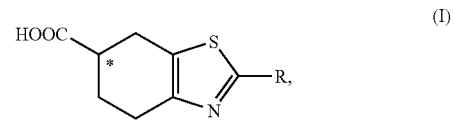

wherein R is a protected amino group and the asterisk * denotes the stereogenic carbon atom, to obtain a compound of formula (III) as the individual (S) enantiomer

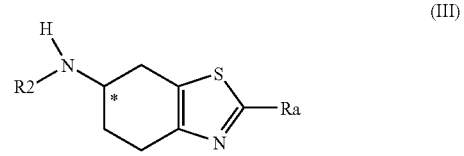

wherein Ra is an free or protected amino group, $R_2$ is hydrogen or a group $R_3$—OR—CO—, wherein $R_3$ is straight or branched $C_1$-$C_4$ alkyl and the asterisk * has the meaning defined above; and (d) alkyating the compound of formula (III) to obtain a compound of formula (IV)

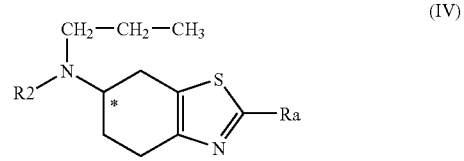

wherein Ra, $R_2$ and the asterisk * are as defined above.

11. The process of claim 10, further comprising the step of converting the compound of formula (IV) to a pharmaceutically acceptable salt thereof, to obtain pramipexole, or a pharmaceutically acceptable salt thereof.

12. The process of claim 10, further comprising the step of:
(e) optionally removing the protective group from the primary amino group, or of the $R_3$—OR—CO— group, or of the primary amino group and of the $R_3$—OR—CO— group, from the secondary amino group.

13. The process of claim 1, further comprising the step of converting the acid of formula (I), either as the (R) or (S) enantiomer, to a salt thereof.

* * * * *